United States Patent
Dey et al.

(10) Patent No.: US 11,354,591 B2
(45) Date of Patent: Jun. 7, 2022

(54) IDENTIFYING GENE SIGNATURES AND CORRESPONDING BIOLOGICAL PATHWAYS BASED ON AN AUTOMATICALLY CURATED GENOMIC DATABASE

(71) Applicant: International Business Machines Corporation, Armonk, NY (US)

(72) Inventors: Sanjoy Dey, White Plains, NY (US); Achille B. Fokoue-Nkoutche, White Plains, NY (US); William S. Spangler, San Martin, CA (US); Ping Zhang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 868 days.

(21) Appl. No.: 16/157,660

(22) Filed: Oct. 11, 2018

(65) Prior Publication Data
US 2020/0118040 A1 Apr. 16, 2020

(51) Int. Cl.
*G06N 20/00* (2019.01)
*G06N 5/02* (2006.01)
*G06F 16/22* (2019.01)
*G16B 20/00* (2019.01)
*G16B 50/30* (2019.01)
*G16B 40/00* (2019.01)

(52) U.S. Cl.
CPC ............. *G06N 20/00* (2019.01); *G06F 16/22* (2019.01); *G06N 5/022* (2013.01); *G16B 20/00* (2019.02); *G16B 40/00* (2019.02); *G16B 50/30* (2019.02)

(58) Field of Classification Search
None
See application file for complete search history.

(56) References Cited

U.S. PATENT DOCUMENTS

| | | | |
|---|---|---|---|
| 6,947,846 | B2 | 9/2005 | Quake et al. |
| 7,243,112 | B2 | 7/2007 | Qu et al. |
| 7,542,947 | B2 | 6/2009 | Guyon et al. |
| 8,364,665 | B2 | 1/2013 | Su et al. |
| 2011/0125734 | A1 | 5/2011 | Duboue et al. |
| 2013/0166599 | A1 | 6/2013 | Kupershmidt et al. |
| 2018/0095969 | A1 | 4/2018 | Jung et al. |

FOREIGN PATENT DOCUMENTS

WO WO2013/011479 A2 1/2013

OTHER PUBLICATIONS

Chen, Xi, and Hemant Ishwaran. "Random forests for genomic data analysis." Genomics 99.6 (2012): 323-329.*
Kohane, Isaac S. "Using electronic health records to drive discovery in disease genomics." Nature Reviews Genetics 12.6 (2011): 417-428.*
Edgar, Ron et al., "Gene Expression Omnibus: NCBI gene expression and hybridization array data repository", Oxford University Press, Nucleic Acids Research, 2002, vol. 30, No. 1, pp. 207-210.
Gundersen, Gregory W. et al., "GEN3VA: aggregation and analysis of gene expression signatures from related studies", BMC Bioinformatics (2016) 17:461, Nov. 15, 2016, 12 pages.
Gundersen, Gregory W. et al., "GEO2Enrichr: browser extension and server app to extract gene sets from GEO and analyze them for biological functions", Bioinformatics 31(18), 2015, May 13, 2015, pp. 3060-3062.
High, Rob, "The Era of Cognitive Systems: An Inside Look at IBM Watson and How it Works", IBM Corporation, Redbooks, Dec. 12, 2012, 16 pages.
Wang, Zichen et al., "Extraction and analysis of signatures from the Gene Expression Omnibus by the crowd", Nature Communications 7:12846, Sep. 26, 2016, 11 pages.
Yuan, Michael J., "Watson and healthcare, How natural language processing and semantic search could revolutionize clinical decision support", IBM Corporation, IBM developerWorks, http://www.IBM.com/developerworks/industry/library/ind-watson/, Apr. 12, 2011, 14 pages.
Zhu, Yuelin et al., "GEOmetadb: powerful alternative search engine for the Gene Expression Omnibus", Bioinformatics Applications Note, vol. 24 No. 23, 2008, pp. 2798-2800.

* cited by examiner

*Primary Examiner* — G Steven Vanni
(74) *Attorney, Agent, or Firm* — Stephen J. Walder, Jr.; Kelsey Skodje

(57) ABSTRACT

Mechanisms are provided to implement a genomic database curation (GDC) system. The GDC system generates a ground truth database based on a training subset of datasets from an uncurated large scale genomic database, and label metadata for the training subset. The GDC system trains at least one classification engine of the GDC system based on the training subset and the ground truth database at least by performing a machine learning operation on the at least one classification engine. The GDC system automatically applies the at least one trained classification engine on the uncurated large scale genomic database to generate an automatically curated large scale genomic database. A meta-classifier engine generates an output specifying at least one of significant gene signatures or gene pathways for at least one of diseases or drug agents based on the automatically curated large scale genomic database.

20 Claims, 6 Drawing Sheets

IDENTIFYING GENE SIGNATURES AND CORRESPONDING BIOLOGICAL PATHWAYS BASED ON AN AUTOMATICALLY CURATED GENOMIC DATABASE

BACKGROUND

The present application relates generally to an improved data processing apparatus and method and more specifically to mechanisms for identifying gene signatures and corresponding biological pathways on large scale gene expression datasets.

A gene signature, or gene expression signature, is a single or combined group of genes in a cell with a uniquely characteristic pattern of gene expression that occurs as a result of an altered or unaltered biological process or pathogenic medical condition. Activating pathways in a regular physiological process or a physiological response to a stimulus results in a cascade of signal transduction and interactions that elicit altered levels of gene expression, which is classified as the gene signature of that physiological process or response. The clinical applications of gene signatures breakdown into prognostic, diagnostic, and predictive signatures. The phenotypes that may theoretically be defined by a gene expression signature range from those that predict the survival or prognosis of an individual with a disease, those that are used to differentiate between different subtypes of a disease, to those that predict activation of a particular pathway. Ideally, gene signatures can be used to select a group of patients for whom a particular treatment will be effective.

The Gene Expression Omnibus (GEO) repository, at the National Center for Biotechnology Information (NCBI), archives and freely distributes high-throughput molecular abundance data, predominantly gene expression data generated by DNA microarray technology. The database has a flexible design that can handle diverse styles of both unprocessed and processed data in a MIAME—(Minimum Information About a Microarray Experiment) supportive infrastructure that promotes fully annotated submissions. GEO currently stores approximately a billion individual gene expression measurements, derived from over 100 organisms, submitted by over 1,500 laboratories, addressing a wide range of biological phenomena. To maximize the utility of these data, several user-friendly Web-based interfaces and applications have been implemented that enable effective exploration, query, and visualization of these data, at the level of individual genes or entire studies.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to configure the at least one processor to implement a genomic database curation system. The method comprises the genomic database curation (GDC) system operating to generate, by the GDC system, a ground truth database based on a training subset of datasets from an uncurated large scale genomic database, and label metadata for the training subset. The method further comprises training, by training logic of the GDC system, at least one classification engine of the GDC system based on the training subset and the ground truth database at least by performing a machine learning operation on the at least one classification engine, to thereby generate at least one trained classification engine. Moreover, the method comprises automatically executing, by the GDC system, the at least one trained classification engine on the uncurated large scale genomic database to generate an automatically curated large scale genomic database. Furthermore, the method comprises generating, by a meta-classifier engine, an output specifying at least one of significant gene signatures or gene pathways for at least one of diseases or drug agents based on the automatically curated large scale genomic database.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1:
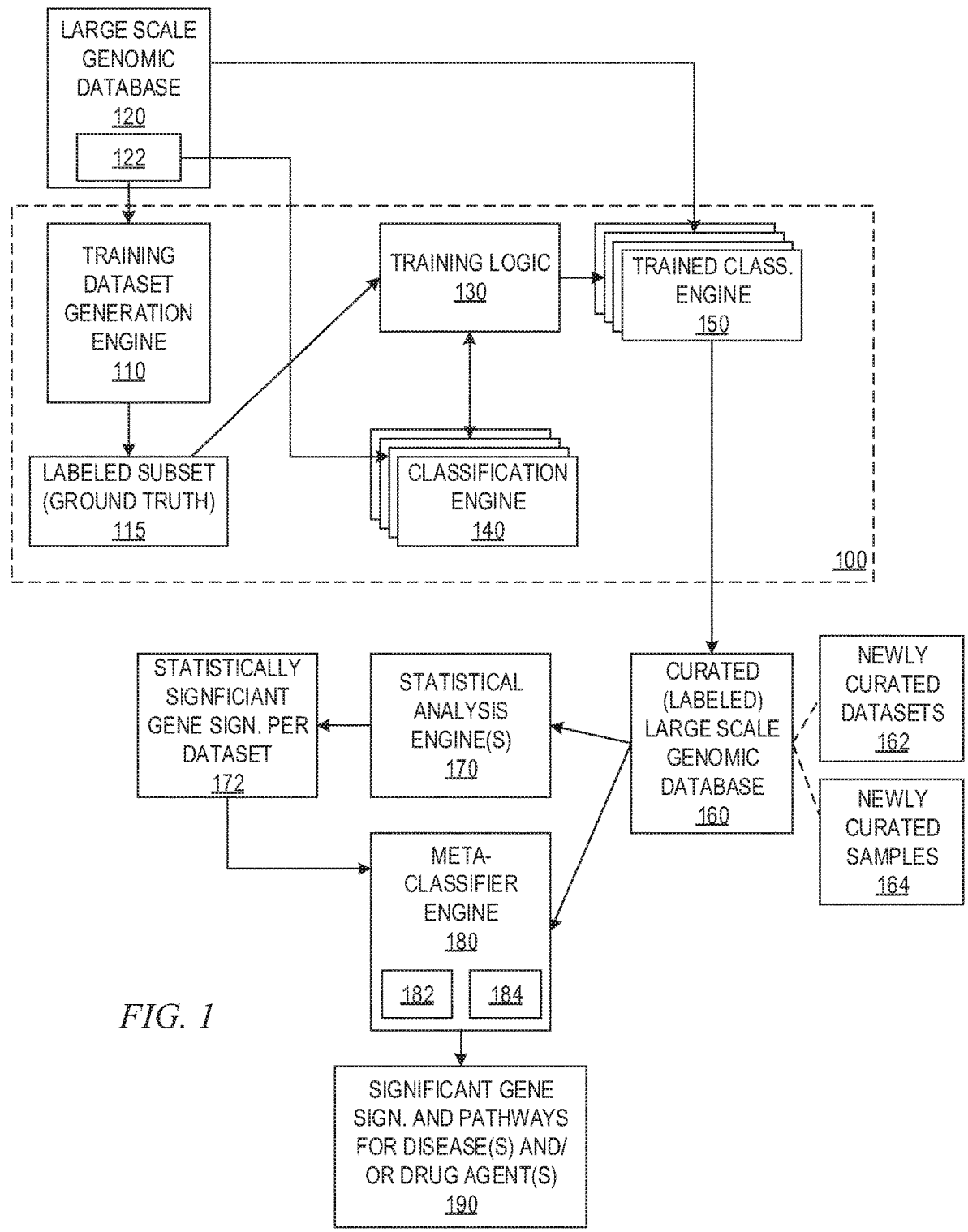
FIG. 1 is an example block diagram illustrating the primary functional operational elements of a genomic database curation (GDC) system in accordance with one illustrative embodiment.

Finding gene expression signatures and their corresponding biological pathways from many publicly available datasets is an important issue in the modern health industry. Such gene expression and the related pathways can reveal the underlying disease mechanism. Therefore, such genes and pathways can eventually be targeted for designing effective interventions to treat the disease.

While the Gene Expression Omnibus (GEO) and other databases of gene expression data are significant tools to aid in addressing this issue, curating the submitted datasets and performing meta-studies on such datasets, such as by combining the individual datasets for a particular disease, drug agent, or the like, is a challenging task given the voluminous amount of data, the differences in sources of such datasets, and the complexity of the potential associations between such datasets. Previous approaches mainly focus such curation of GEO datasets on manual processes in which human experts must perform their own searches of these large scale datasets to identify a particular disease or drug agent and find gene expression signatures in the large scale datasets that have some correspondence with the particular disease or drug agent. This being a manual process means that it is very time consuming and error prone with a high potential of some gene expression signatures and/or drug agent associations with diseases being missed in the process. Being a manual process, the process is only applicable for finding the significant genes from only a few sets of GEO datasets of interest, often containing less than five GEO datasets.

The mechanisms of the illustrative embodiments automatically integrate a large number of GEO datasets in order to find the significant genes that are common in these datasets. Specifically, a two-stage machine learning operation is provided in which, as part of a first stage of machine learning, the individual GEO datasets are curated from free texts available in the GEO metadata to identify the disease onset or drug agent under consideration. In a second stage of operation, a hierarchical random-effect model for predicting the significant genes present in multiple studies with the same disease phenotype is developed. Furthermore, the illustrative embodiments identify the pathways consisting of multiple genes that are associated with the same disease phenotype.

The illustrative embodiments provide an improved computing tool, referred to herein as the genomic database curation (GDC) system, for automatically curating, without human intervention, a large scale genomic database having a large number of gene expression signature datasets, such as the GEO database and its corresponding datasets. The genomic database comprises datasets which represent genomic studies (hereafter referred to as simply "studies") performed by contributors to the genomic database. The genomic database may receive datasets from a plurality of different sources such that the genomic database serves as a central data warehouse of genomic study data. Each dataset, or study, in the genomic database may comprise metadata and corresponding descriptions of the study, samples contained in the study, and the like, as is generally known in the art, such as in the case of the GEO database discussed above.

For example, the metadata information of a GEO dataset contains free text, such as the purpose of the study, experimental protocols used, and so on, submitted by independent researchers. However, such metadata lacks any standard formats and database usage. This metadata information is thus, not easily machine readable and therefore requires a specialized computation tool, as provided by the natural language processing mechanisms of the illustrative embodiments, to extract relevant information from the free text. Moreover, the metadata information associated with the samples contain free-texts which are helpful to determine the categories of disease onset or drug responses. For disease conditions, the samples that have those disease states and the samples that are controls are identified via the mechanisms of the illustrative embodiments. For the drug states, the drug name, the dosage information, and IC50 score after a few hours (typically, with an interval of 6 or 12 hours) are recorded for each sample and identified via the mechanisms of the illustrative embodiments.

The improved computing tool of the illustrative embodiments, i.e. the GDC system, comprises one or more classification engines, training logic for training the one or more classification engines, and gene association statistical analysis logic. The GDC system further operates in conjunction with a meta-classifier engine that operates on a curated genomic database generated by the GDC system, to identify significant genetic pathways and gene signatures associated with specific diseases and/or drug agents. The classification engines of the GDC system may be implemented as neural network models, inference engines, or the like, which are trained to infer a classification from features extracted from an input dataset of the genomic database. Each classification engine may be built and configured to extract particular features from a genomic database dataset that is input to the classification engine, and process these features in order to infer or predict a classification for the particular dataset. For example, the one or more classification engines, in accordance with one illustrative embodiment, may comprise a first classification engine that is configured and trained to classify inputs into classes of disease states, or a non-disease state, thereby generating a disease class label for the dataset. A first level of classification models may be built to check whether the study associated with the input dataset belongs to a particular disease or drug, e.g., whether a dataset is for lung cancer or not. Therefore, there may be a different classification engine for each potential disease with the output of each classification engine being a binary output indicating whether the input dataset (study) is for the particular disease or not.

A second classification engine may be configured and trained to classify a study corresponding to the dataset to be a drug agent study or a non-drug agent study, to thereby generate a binary drug agent class label. Similar to the first level of classification models, there may be different classification engines for different drug agents which may check whether a particular study involved a particular drug agent or not.

A third classification engine may be configured and trained to identify whether the particular sample referenced in the dataset has the corresponding disease state or not (is a control), to thereby generate a disease state binary class label. Note that the diseases can be of multi-state containing multiple phenotypes of the same disease, e.g., different subtypes of Lymphoma.

One or more fourth classification engines may be configured and trained to evaluate samples at each time point after a drug administration (also referred to as the "drug state"). There may be a separate classification engine for each time point after the drug administration.

The labels generated by the various classification engines may be combined as metadata that is logically coupled to (such as via pointers or other computer constructs that provide associations between data), or integrated in, the corresponding dataset such that the dataset becomes a curated or labeled dataset. In the curated or labeled dataset, the labels define the classes of data present within the dataset, e.g., the study associated with the dataset is a lung cancer study, the study is for a drug agent, the sample in the study has the disease state (e.g., lung cancer in this case), and the study has a $IC_{50}$ of X at an interval of 6 hours after the drug state (administration of the drug agent).

The training of the one or more classification engines of the cognitive computing system uses a relatively small subset of the genomic database. The small subset of the genomic database is manually curated by a subject matter or domain expert. For example, the curated GEO datasets may contain a small subset (4138 datasets) of the whole GEO database (~80000 datasets). Thus, for this subset of manually curated datasets, all the information, such as name of disease-state or drug agent, the sample's phenotype of diseases (control vs. different disease subtypes), the sample's condition after each time point for drug agents, etc. are clearly identified in a SQLite database. Therefore, all of this information can be retrieved using queries directed to the database. Then, the curated datasets are used by the mechanisms of the illustrative embodiments to build and train the classification models by using the subset of manually curated datasets as the training input and the correct labels associated with the datasets as the ground truth data structures for training the classification models of the cognitive computing system. In other words, the ground truth data structure comprises the correct label data for various pre-defined classifications as generated by the human subject matter expert, i.e. the correct labels (it should be appreciated that the term "label" used herein refers to the data or metadata specifying the classification(s) associated with the dataset) which the particular classification engines are being trained to be able to generate for genomic database datasets. These labels (metadata) are correlated with the natural language text version of the selected dataset, which comprises a metadata portion and a corresponding sample's descriptions portion. Thus, for example, the ground truth curated GEO datasets may specify for each dataset whether or not the corresponding study was for particular disease states or not, whether or not the study was for a drug agent or not, whether a particular sample of the study had the disease state or not, and also labels for time points after the drug state, e.g., an $IC_{50}$ score after a predetermined time period after administration of a drug agent. $IC_{50}$ refers to the half maximal inhibitory concentration, which is a measure of the potency of a substance in inhibiting a specific biological or biochemical function. The predetermined time period may be specified as a particular interval, or specific time points, after administration of the drug agent, e.g., a 6 hour or 12 hour interval.

Using a machine learning approach, the natural language or free text version of the selected datasets is input to the particular classification engines which process the natural language or free text input and generate a corresponding classification output, e.g., a vector output having vector slots for each of the predefined classifications that the particular classification engine classifies input into. Each vector slot in the vector output may comprise a numerical value indicative of the probability that the input is properly classified into the corresponding class. The classification output is compared to the corresponding ground truth classification to determine if the classification engine generated a correct classification output. The difference between the ground truth and the classification output may be used to drive a modification of the operational parameters of the particular classification engine, e.g., changing weights of intermediate nodes of the neural network models or the like, to thereby minimize the error or loss in the classification output generated by the classification engine. This process is performed iteratively until the error or loss is equal to or below a predetermined threshold at which point the classification engine is determined to have been trained.

After having built and trained the classification engine(s), the classification engine(s) are automatically executed on the complete large scale genomic database, e.g., the complete GEO database, comprising all the datasets in the large scale genomic database. Natural language processing may be performed on each of the uncurated datasets in the genomic database to extract features from the free-text of the metadata and sample information, for example, and these features may be fed into the trained classification engine(s) to thereby classify the input uncurated dataset and generate corresponding label metadata. The label metadata may then be stored in association with the uncurated dataset to thereby generate a curated dataset.

In other words, a small curated subset of the genomic database is used to train the classification engines which may then be used to automatically label the entire large scale genomic database. Thus, through processing each dataset in the complete genomic database via the trained classification engine(s), each dataset is associated with corresponding pre-determined class labels, thereby automatically generating a curated or labeled large scale genomic database. The curated or labeled large scale genomic database may then be analyzed for specific disease states and drug agents to identify statistically significant gene associations corresponding to these specific disease states and drug agents.

Thus, for example, for each dataset, the trained classification engine(s) identify and label the dataset as to whether the corresponding study was for a specific disease state and/or a specific drug agent. In addition, the labels indicate whether the sample had the disease state (disease sample) or did not have the disease state (control sample). Based on these labels, subsets of curated datasets that correspond to a particular disease and/or drug agent, as well as whether or not the corresponding sample was a disease sample or a control, may be generated and then statistically analyzed to identify statistically significant gene associations with the particular disease and/or drug agent. The identification of statistically significant gene associations in gene study databases is generally known in the art and thus, a more detailed explanation of the identification of statistically significant gene associations is not included herein. Examples of types of statistical analysis techniques that may be used to identify statistically significant gene associations include Fishar's exact test, Chi-square test with multiple hypothesis tests, and GEO2Enrichr.

After identifying the statistically significant gene associations in each of the separate datasets of the curated large scale genomic database, a meta-classifier engine, implementing one or more hierarchical random effect models, is used to combine the separate datasets and thereby merge the individual signals of gene signatures of the individual datasets taking into account the individual statistical scores of each of the genes or gene signatures on each dataset and weighting them based on the variance on each dataset. In addition, hierarchical random-effect models are also implemented for each of the biological pathways, i.e. gene groups, in order to find significant pathways and associations of the gene signatures with these biological pathways. More specifically, we use the gene set enrichment tools first to determine the statistical significance and variance of each pathway within each GEO datasets and then use the same hierarchical random-effect model to combine the individual values of each dataset for a given pathway. It should be noted that the terms "gene", "gene associations", and "gene signature" are used synonymously herein for representing a single gene while a "pathway" refers to a group or plurality of genes.

The meta-classifier engine generates an output indicating the significant pathways and gene signatures present in the genomic database for specific diseases and/or drug agents. In addition, the output from the classification models may be provided for viewing and/or other analysis, i.e. the newly curated datasets and newly curated samples may be output for view and/or analysis. These newly generated curated datasets can further be used by any domain expert to analyze independently for understanding disease mechanism further. That is, by viewing and/or analyzing the newly curated datasets via a graphical user interface and/or automated analysis mechanisms, the obtained genes and pathways for a particular disease may be used by domain experts for understanding the disease and drug mechanism in greater detail. Then, the obtained knowledge can be utilized for designing interventions which can target those genes and pathways to alter the disease outcome.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for automated curation of large scale genomic databases to generate curated or labeled genomic databases that may be used to perform analysis to identify statistically significant gene associations, gene signatures, and pathways for specific diseases and/or drug agents. The illustrative embodiments provide mechanisms for building and training classification engines, which may implement one or more neural network models or other types of inference engines, to perform various classifications on input genomic database datasets. The training of such classification engines comprises the curation of a small selected subset of datasets from the genomic database as a ground truth which is used to train the classification engines. Once trained, the classification engines are executed on the complete genomic database to generate a curated or labeled genomic database which is then analyzed using statistical analysis techniques to identify statistically significant gene associations with specific disease states and/or drug agents. A meta-classifier engine is then applied to identify significant genetic pathways and gene signatures for particular disease states and/or drug agents. This information, along with the newly curated genomic database and its labeled datasets may be provided as output, such as via a graphical user interface or the like, for viewing as well as for further analytics and cognitive computer processing.

FIG. 1 is an example block diagram illustrating the primary functional operational elements of a genomic database curation (GDC) system in accordance with one illustrative embodiment. It should be appreciated that the particular elements shown in FIG. 1 are implemented as specific logic within one or more specifically configured computing devices that are specifically configured by this logic to perform the corresponding functions. Once the one or more computing devices are specifically configured with the logic of the particular elements shown in FIG. 1, they become specialized computing devices specifically configured to perform the functions attributed to those elements, as described herein, and are not generic computing devices performing merely generic, routine, well-understood, or conventional computer functions. The present invention provides new improvements in functionality of these computing devices through the configuration of these computing devices to implement the particular elements shown in FIG. 1, which are directed to solving the previously described problems with regard to computerized curation of large scale genomic databases and the meta-classification of the data present in such large scale genomic databases for identifying significant genetic pathways and gene signatures for diseases and/or drug agents.

As shown in FIG. 1, in accordance with one illustrative embodiment, a genomic database curation (GDC) system 100 comprises a training dataset generation engine 110 through which a training subset 122 of datasets present in a large scale genomic database 120 is selected and labeled with metadata specifying correct classifications for the datasets present in the training subset 122, to thereby generate a curated subset or ground truth dataset 124 comprising natural language or free text of the datasets, and metadata of the datasets, in the selected training subset 122, and the corresponding label metadata. The natural language or free text, e.g., the sample description, of the dataset in the large scale genomic database 120 may comprise various types of information regarding the nature, parameters, and results of the gene study corresponding to the dataset. The metadata of a dataset in the large scale genomic database 120 may comprise metadata that may be provided as natural language or free text, or as structured data, that may specify various information describing the study including the purpose of the study, experimental protocols, drug agent information, disease condition information etc. For example, for disease condition metadata, the metadata may specify the name of the disease, the samples that have those disease states and identification of control samples. For the drug agent metadata, the metadata may specify the drug name, the dosage information, and the $IC_{50}$ scores after certain time periods from the administration of the drug agent, for each sample.

Both the natural language or free text portion, e.g., the sample description, of the dataset and the metadata of the dataset do not have any standard formats or database usage. That is, because the datasets are generated by different sources, e.g., different research entities, the datasets may have vastly different ways of representing the natural language/free text portion and the metadata portion, dependent upon the particular sources providing the dataset. Thus, this information is not readily machine readable and requires a specialized computing tool to extract the relevant information from the natural language/free text portion and metadata portion. The metadata of the study contains information about the purpose of the study, experimental protocols used, etc., but generally does not include the individual sample descriptions (it should be appreciated that a study may comprise multiple samples). On the other hand, the sample description contains free text describing only a particular sample of interest and its relationship with the disease phenotype. Thus, the study and sample information is extracted from the various portions of the datasets for use by the classification engines using the mechanisms of the illustrative embodiments.

The training ground truth genomic database generation engine 110 provides logic for selecting a subset of datasets in the entire large scale genomic database 120 for use in generating a ground truth genomic database 115 for training one or more classification engines 140 of the GDC system 100. This selection may be performed manually by a subject matter expert via a graphical user interface provided by the training ground truth genomic database generation engine 110, or may be performed automatically or semi-automatically by the training ground truth genomic database generation engine 110. For an embodiment in which the selection is performed automatically or semi-automatically, logic in the training ground truth genomic database generation engine 110 may select datasets from the large scale genomic database 120 based on pre-specified criteria in order to obtain a training ground truth genomic database 115 that represents the variety of different disease states and drug agents that may be present in the overall complete large scale genomic database 120. That is, a sufficient number of datasets for each type of drug agent and disease state may be selected by performing a database search and finding datasets whose metadata mentions the disease states and drug agents, and selecting a subset of each to be included in the training ground truth genomic database 115. In a semi-automatic selection process, the selected subset of datasets may be presented to a subject matter expert for confirmation via a graphical user interface before including them into the training ground truth genomic database 115.

Whether the subset of datasets 122, i.e. the training subset 122, selected for inclusion in the training ground truth genomic database 115 is selected automatically, semi-automatically, or manually, the selected datasets may be presented to a subject matter expert for manual curation/labeling by generating classification labels manually for each dataset. These labels may be presented to the subject matter expert via a graphical user interface as selectable options when viewing a particular dataset to thereby associate with the dataset the correct label metadata defining the classifications associated with the study corresponding to the dataset, based on the subject matter expert's expertise. This label metadata may be stored either in the metadata of the dataset which is included in the training ground truth genomic database 115, or may be stored as a separate data structure linked to the dataset. For example, the subject matter expert may view the dataset, determine that the study is for a particular disease state and select a corresponding disease state label from a selectable option, e.g., a menu, button, or the like in the graphical user interface, determine that the study includes a drug agent and select a corresponding binary or class label for indicating the drug agent, determine that a sample in the study had the disease state or was a control and select the corresponding binary class label, as well as determine drug potency labels for time points after administering the drug agent. Each of these labels may be selected by the subject matter expert via the graphical user interface and the corresponding label metadata added to the metadata associated with the dataset, which is then included in the training ground truth genomic database 115.

This process for generating the training ground truth genomic database 115 may be repeated for each selected dataset in the training subset 122. As noted above, the datasets that are included in the training ground truth genomic database 115 represent only a small training subset 122 of the entire large scale genomic database 120. For example, in one example embodiment, the large scale genomic database 120 may comprise approximately 80,000 datasets or more, while the training subset 122 may comprise only approximately 4000 datasets. The 4000 datasets are curated/labeled by the subject matter expert and compiled into the training ground truth genomic database 115 which may be accessed via database query mechanisms.

The training ground truth genomic database 115 and the corresponding subset 122 of datasets selected from the large scale genomic database 120, are used by the training logic 130 of the GDC system 100 to train one or more classification engines 140 to perform classification of datasets in the large scale genomic database 120. That is, the original selected training subset 122 of datasets may be input to the corresponding classification engine(s) 140 being trained, and the training ground truth genomic database 115 may be accessed by the training logic 130. The one or more classification engines 140 are executed on each dataset in the training subset 122 of datasets to generate a corresponding classification prediction/inference output. For example, the classification engine(s) 140 may perform various natural language processing operations on the natural language or free text portions of the selected training subset 122, e.g., lemmatization, stemming, normalization, and other natural language processing operations, to generate word embedded features from n-grams. The word embedded features may be processed by the neural network models of the classification engine(s) 140 to generate the corresponding outputs of the classification engine(s) 140. The classification engine(s) 140 perform a logistic regression on the word embedded features.

The classification prediction/inference output may then be provided to the training logic 130 which compares the output generated by the classification engine 140 to the corresponding ground truth information for the input dataset from the training ground truth genomic database 115. The training logic 130 may then determine an appropriate modification to operational parameters of the classification engine 140 to reduce an error or loss between the output generated by the classification engine 140 and the ground truth information for the dataset. This process may be repeated iteratively for other datasets in the training subset 122 until the error or loss is equal to, or lower than, a predetermined threshold amount of error/loss.

Once the one or more classification engines 140 are trained using the training subset 122 of the large scale genomic database 120, the resulting trained classification engines 150 are executed on the full large scale genomic database 120 to thereby generate label metadata for the various datasets present within the large scale genomic database 120. The generated label metadata may be integrated into the metadata of the datasets within the large scale genomic database 120 or otherwise provided as a data structure that is linked to the corresponding dataset within the large scale genomic database 120 to thereby generate a curated or labeled large scale genomic database 160. The curated or labeled large scale genomic database 160 comprises newly curated datasets 162 and newly curated samples 164.

Thus, through processing each dataset in the complete genomic database 120 via the trained classification engine(s) 150, each dataset is associated with corresponding predetermined class labels, thereby automatically generating a curated or labeled large scale genomic database 160. The curated or labeled large scale genomic database 160 may then be analyzed for specific disease states and drug agents to identify statistically significant gene associations corresponding to these specific disease states and drug agents. For example, for each dataset, the trained classification engine(s) 150 identify and label the dataset as to whether the corresponding study was for a specific disease state and/or a specific drug agent. In addition, the labels indicate whether the sample had the disease state (disease sample) or did not have the disease state (control sample).

Based on these labels, subsets of curated datasets from the curated or labeled large scale genomic database 160, which correspond to a particular disease and/or drug agent, as well as whether or not the corresponding sample was a disease sample or a control, may be generated and then statistically analyzed to identify statistically significant gene associations, such as may be specified in the sample descriptions of the particular dataset, with the particular disease and/or drug agent. The statistical analysis may be performed using one or more statistical analysis logic engine(s) 170 which, as mentioned previously, may include various types of statistical analysis techniques such as Fishar's exact test, Chi-square test with multiple hypothesis tests, and GEO2Enrichr, as examples.

After the statistical analysis logic engine(s) 170 identify the statistically significant gene associations in each of the separate datasets of the curated large scale genomic database 160, a meta-classifier engine 180, implementing one or more hierarchical random effect models 182, is used to combine the separate datasets and thereby merge the individual signals of gene signatures of the individual datasets taking into account the individual statistical scores of each of the genes or gene signatures on each dataset and weighting them based on the variance on each dataset. In addition, hierarchical random-effect models 184 are also implemented for each of the biological pathways, i.e. gene groups, in order to find significant pathways and associations of the gene signatures with these biological pathways.

The meta-classifier engine 180 generates an output 190 indicating the significant pathways and gene signatures present in the genomic database for specific diseases and/or drug agents as identified by the hierarchical random-effect models 182 and 184. In addition, the output from the trained classification models 150, e.g., the newly curated datasets 162 and newly curated sample information 164 of the curated or labeled large scale genomic database 160, may be provided for viewing and/or other analysis.

It should be appreciated that the Meta-classifier engine 180 may be built in many different ways. In one illustrative embodiment, the meta-classifier engine 180 may be built to combine the individual datasets into a large new pool of datasets containing all the samples of all datasets and the genes that are common in all datasets. Then, statistical analysis is performed on the combined datasets, similar to the statistical analysis performed on the individual datasets. This is referred to as an "early integration", since the datasets are merged early in the dataset analysis process. However, this type of early integration is very difficult, since each dataset may contain different sets of genes, therefore taking the common genes will reduce the gene sets significantly. Moreover, each dataset may have different experimental setup which will lead to different bias in the experiments.

An alternative, and more efficient, approach is to integrate signals of genes present in datasets rather than integrate the datasets themselves. This is referred to as "information integration." In the alternative "information integration" approach, the information is extracted from each dataset first using a statistical analysis and then a machine learning technique (e.g., hierarchical mixed-effect model) is used to combine the information present in each dataset. Both approaches or integration techniques for finding genes and pathways that are significantly associated with a particular disease may be used without departing from the spirit and scope of the present invention.

Figure 2:
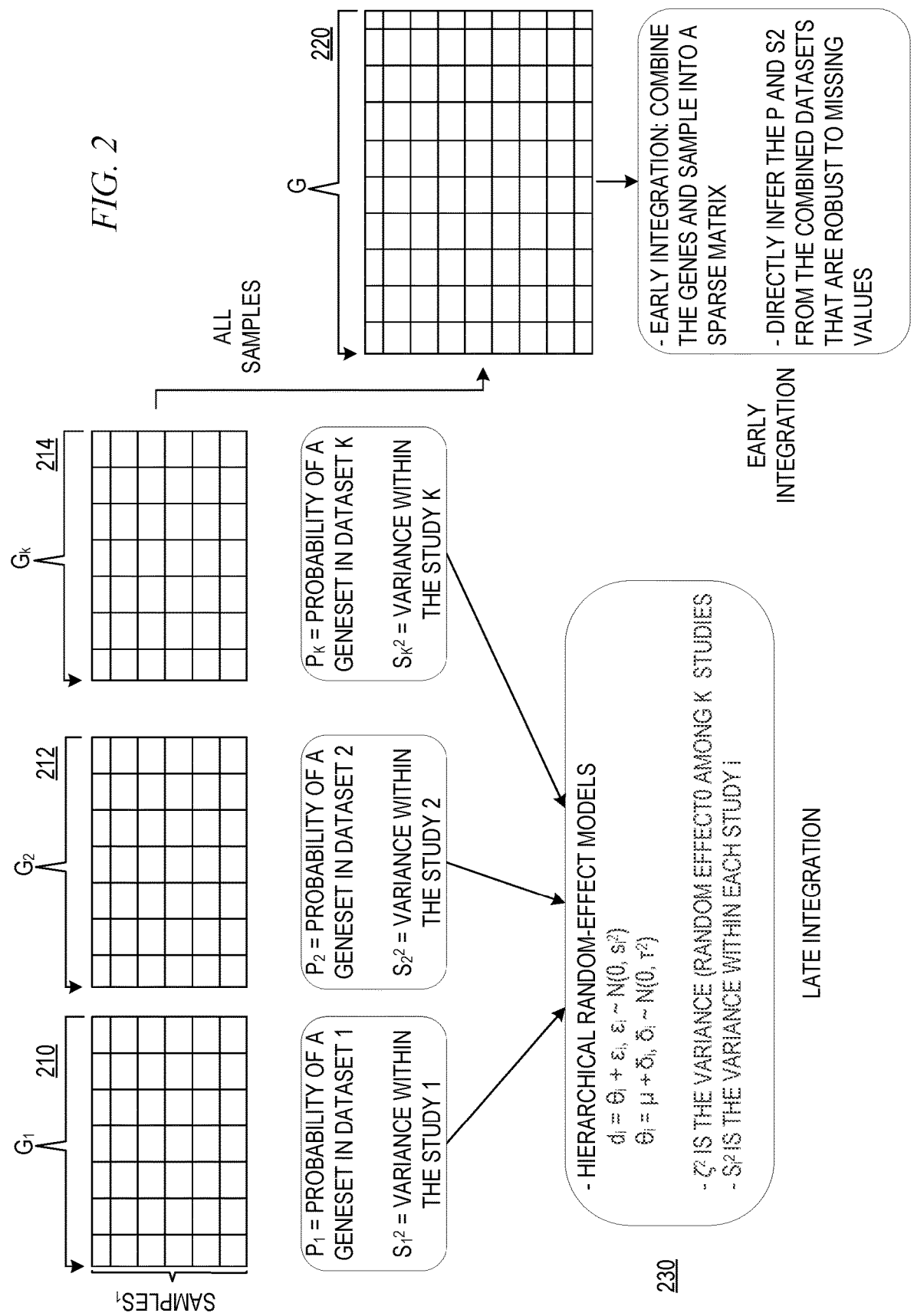
FIG. 2 is an example diagram illustrating an operation of an information integration meta-classifier engine in accordance with one illustrative embodiment.

FIG. 2 is an example diagram illustrating an operation of an information integration meta-classifier engine in accordance with one illustrative embodiment. As shown in FIG. 2, the metaclassifier engine 200 generates sample matrices 210-214 for each study. In the depicted example, the sample matrices 210-214 comprise rows representing the different samples present in the study and columns representing particular gene signatures determined to be "significant" genes by way of applying the statistical analysis. Values in each of the cells of the matrix represent the probability of the particular gene signature in the corresponding dataset for the study. That is, the probability value indicates the probability that the corresponding gene has an association with the particular disease/drug agent of the dataset. This probability value is obtained from the statistical analysis, such as the Ghi-2 test, Fishar's exact test, or the like. Thus, each study $S_1$ to $S_k$ may comprise one or more samples and corresponding probability values for each sample that correspond to gene signatures in a set of gene signatures $G_1$ to $G_k$. It should be noted that the set of gene signatures $G_1$ to $G_k$ may vary from study to study, however in some illustrative embodiments the same set of gene signatures common to all studies may also be utilized, depending on the desired implementation.

Each individual study's sample matrix 210-214 has a corresponding variance within the study $s_1{}^t$ to $s_k{}^2$. The combination of these variances for a particular gene signature within the sample matrices 210-214 provides a variance of the gene signature among the k studies, which may be used to weight the various sample matrix 210-214 samples in a combined matrix 220 comprising all the samples of all the studies and the corresponding weighted probability values for each of the gene signatures in the gene signature set G. The combined matrix 220 combines the genes and samples into a sparse matrix which can be used to directly infer the probability and variance from the combined datasets, such as by using the equations shown in FIG. 2, for example, which are robust to missing values.

Thus, the meta-classifier engine is applied to merge multiple study datasets 210-214 in the labeled large scale genomic database. For example, this merging may involve merging datasets associated with similar diseases, datasets associated with similar drug agents, datasets associated with similar diseases and drug agents, etc. The particular merging may be based on a user's request or query specifying the type of information of interest, e.g., datasets associated with similar drug agents, datasets associated with similar diseases, etc. The meta-classifier engine implements one or more machine learning tools 230, referred to as hierarchical random-effect model(s) 230, which merge individual signals of gene signatures of the individual datasets 210-214. The hierarchical random-effect model(s) 230 take into account the individual score of each gene on each dataset 210-214 and then weights these scores based on the variance on each dataset. This process using the hierarchical random-effect model(s) may also be performed for each pathway in order to find significant pathways. As a result, a combined matrix 220 is generated that comprises the merged datasets where entries in the combined matrix 220 set forth the probabilities and variances of gene signatures and/or pathways with regard to the disease and/or drug agent.

From the probabilities and variances in the combined matrix 220, meaningful associations between bio-entities, e.g., drugs, genes, diseases, etc. can be identified to provide key insights and generate hypotheses, such as in the drug discovery process and disease states. That is, the meta-classifier engine output may be provided to other analysis systems, cognitive computing systems, and the like, to perform operations for assisting human health care providers, researchers, and the like, in performing their functions for assisting patients and/or performing research on genes, drugs, and diseases. These analysis systems, cognitive computing systems, and the like, may utilized predicted associations generated based on the output of the meta-classifier engine to performing their operations. Examples of such predicted associations include drug-gene associations, drug-pathway associations, disease-gene associations, and disease pathway associations. Drug-gene and drug-pathway associations may include, for example, adverse drug and drug repositioning use cases. Disease-gene and disease-pathway associations may include, for example, bio-markers of disease and risk assessment use cases. These associations may be used as further information to cognitive computing systems, analysis systems, and the like, to provide recommendations regarding research, treatments for patients, or other healthcare oriented operations to which specialized computing devices are put.

Thus, the illustrative embodiments provide mechanisms for automatically training one or more classification engines based on a selected subset of datasets from a large scale genomic database. Once trained, the one or more classification engines are applied to the full or complete large scale genomic database to generate a curated or labeled large scale genomic database in which the datasets in the database are labeled with classification labels, such as a disease state class label, a drug agent class label, a disease sample/control sample class label, and a potency class label for time points after administration of a drug, for example. From this labeled large scale genomic database, statistical analysis is separately performed on each dataset to identify significant gene associations in each of the datasets. Thereafter a meta-classifier engine is applied to merge multiple studies, i.e. datasets, in the labeled large scale genomic database, such as merging datasets associated with similar diseases. The meta-classifier engine implements one or more machine learning tools, referred to as hierarchical random-effect models, which merge individual signals of gene signatures of the individual datasets. The hierarchical random-effect model(s) take into account the individual score of each gene on each dataset and then weights these scores based on the variance on each dataset. This process using the hierarchical random-effect model(s) may also be performed for each pathway in order to find significant pathways. As a result, the illustrative embodiments provide a curated or labeled large scale genomic database as well as the identification of significant gene signatures and pathways associated with different diseases and/or drug agents.

Figure 3:
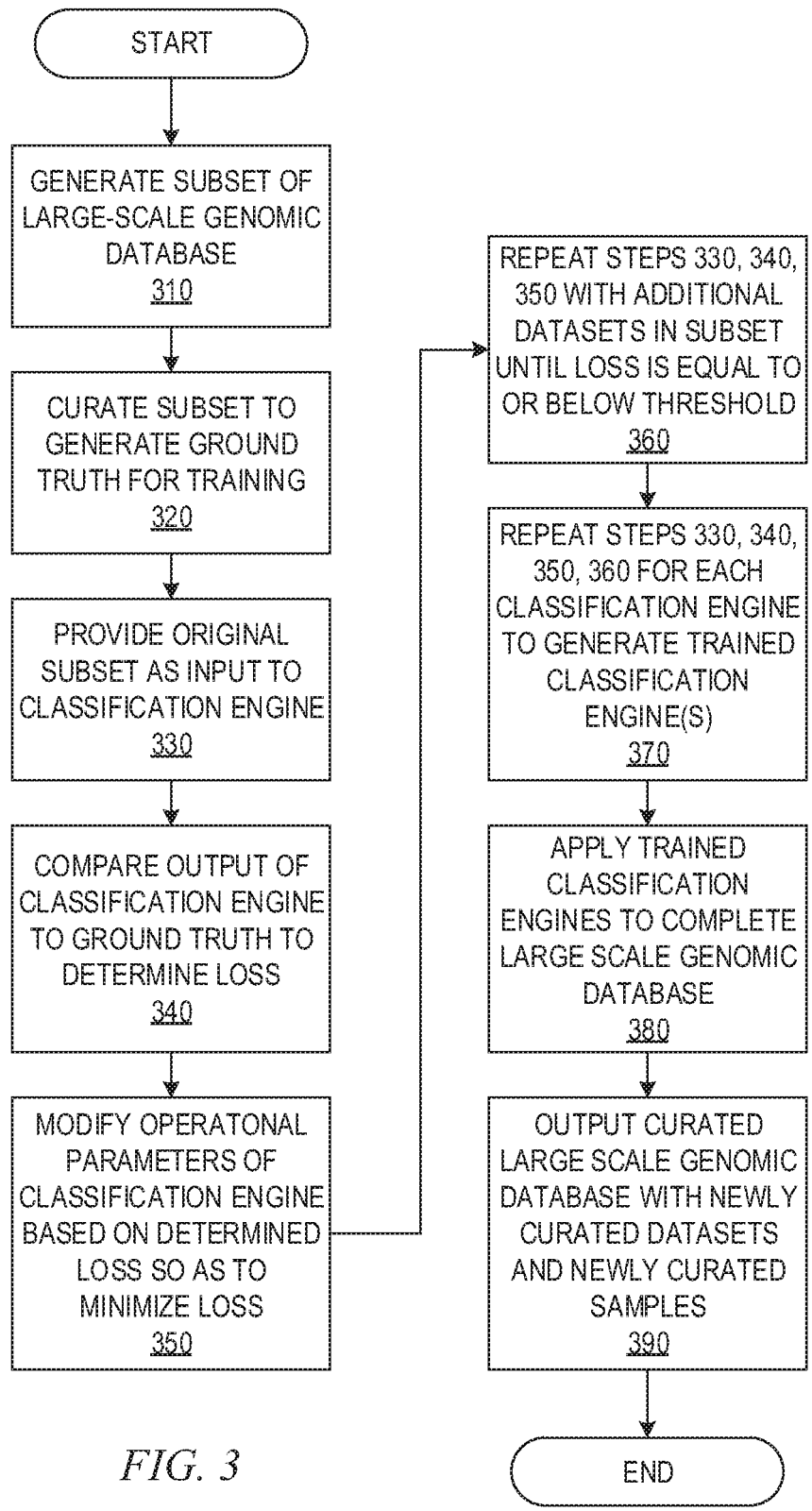
FIG. 3 is an example flowchart outlining an operation of a genomic database curation (GDC) system in accordance with one illustrative embodiment.

FIG. 3 is an example flowchart outlining an operation of a genomic database curation (GDC) system in accordance with one illustrative embodiment. As shown in FIG. 3, the operation starts by generating a subset of datasets from the large-scale genomic database (step 310). The subset of datasets is then curated and labeled by a subject matter expert to generate a ground truth database for training one or more classification engines, e.g., neural network models that classify inputs into one of a plurality of predefined classifications (step 320). The original subset of datasets is input to a classification engine (step 330) which generates an output of a predicted or inferred classification for the input dataset with regard to the particular type of classification that the classification engine performs, e.g., disease state classification, drug agent classification, disease sample/control sample classification, or potency classification at time points, etc.

The output of the classification engine is compared to the ground truth for the particular dataset in the subset input to the classification engine to determine an error or loss (step 340). Based on the identified loss, the operational parameters of the classification engine are modified to minimize the loss, e.g., weights associated with nodes in the neural network model are modified to minimize the loss (step 350). These operations 330-350 are repeated with additional datasets from the subset until the loss in the output of the classification engine is equal to or below a predetermined threshold, at which point the classification engine is considered to have been trained (step 360). This same process of steps 330-360 is repeated for each classification engine to thereby generate trained classification engine(s) (step 370).

Once the classification engines are trained using the subset of the large-scale genomic database and curated subset as a ground truth, the trained classification engines are applied to the complete large scale genomic database to generate a curated large scale genomic database (step 380) which is output (step 390). The operation then terminates.

Figure 4:
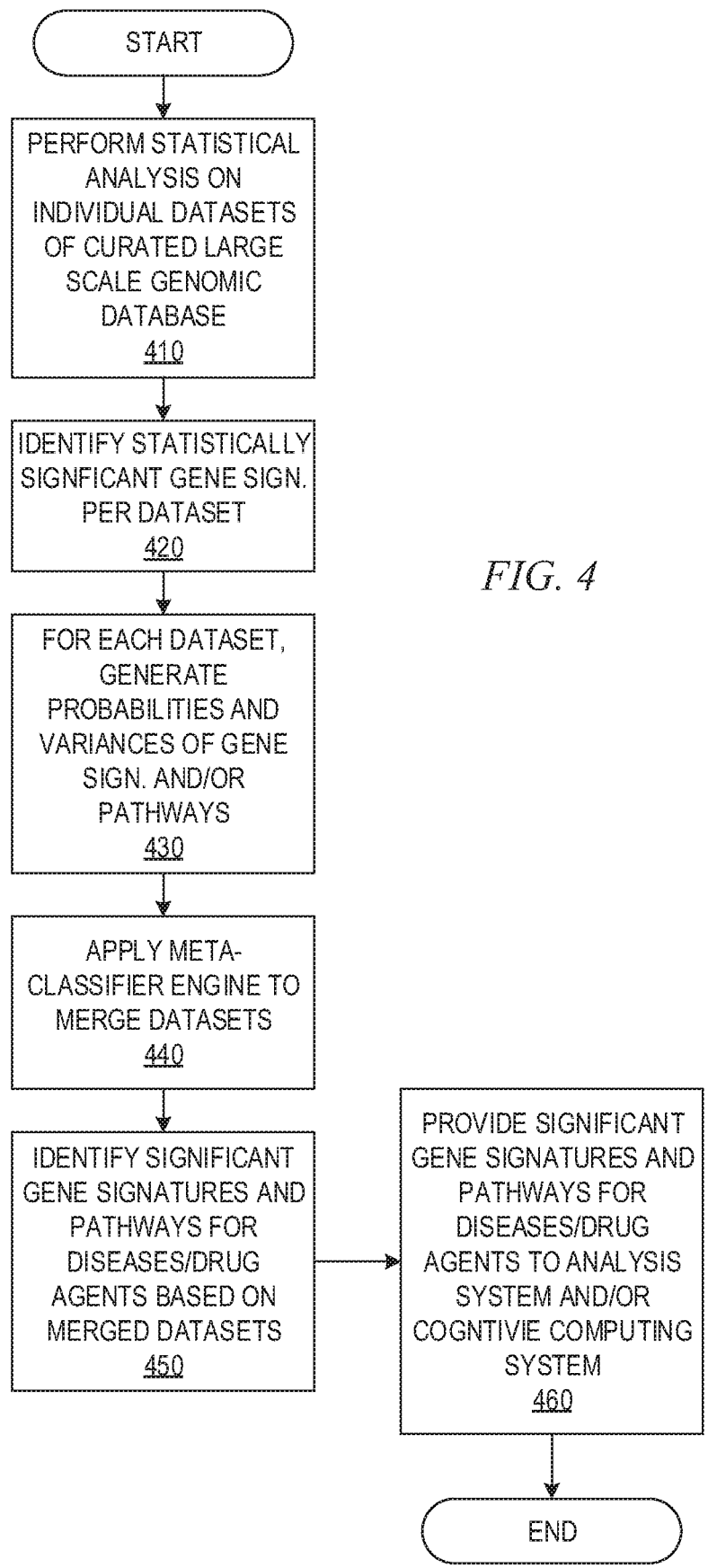
FIG. 4 is an example flowchart outlining an operation for identifying significant gene signatures and pathways for a disease and/or drug agent in accordance with one illustrative embodiment.

FIG. 4 is an example flowchart outlining an operation for identifying significant gene signatures and pathways for a disease and/or drug agent in accordance with one illustrative embodiment. As shown in FIG. 4, the operation starts by performing statistical analysis on individual datasets of the curated large scale genomic database (step 410). Based on the statistical analysis, statistically significant gene signatures are identified per dataset in the large scale genomic database (step 420). For each dataset, probability values and variances for gene signatures and/or gene pathways are generated (step 430) and a meta-classifier engine operates on the datasets to merge datasets, e.g., merge datasets for specific diseases and/or drug agents (step 440). From the merged datasets, significant gene signatures and/or pathways for diseases/drug agents are identified (step 450). The significant gene signatures and/or pathways for diseases/drug agents are provided as additional reference information for use by an analysis system and/or cognitive computing system (step 460). The operation then terminates.

As is clear from the description above, the illustrative embodiments are directed to a new and improved computer tool that assists human beings in the curating of large scale genomic databases as well as provides automated tools for identifying significant gene signatures and pathways for diseases and/or drug agents. As such, the present invention is implemented as at least one of specialized hardware, specialized software executing on hardware, or a combination of specialized hardware and specialized software executing on hardware. In the case of elements of the present invention being implemented as specialized software, it should be appreciated that when the hardware is specifically configured by the specialized software, the hardware is transformed into a different state and represents a specialized computing device that performs non-generic, non-well understood, non-routine, and non-conventional computer functions either in addition to, or in replacement of, the basic functions of the computing device.

Figure 5:
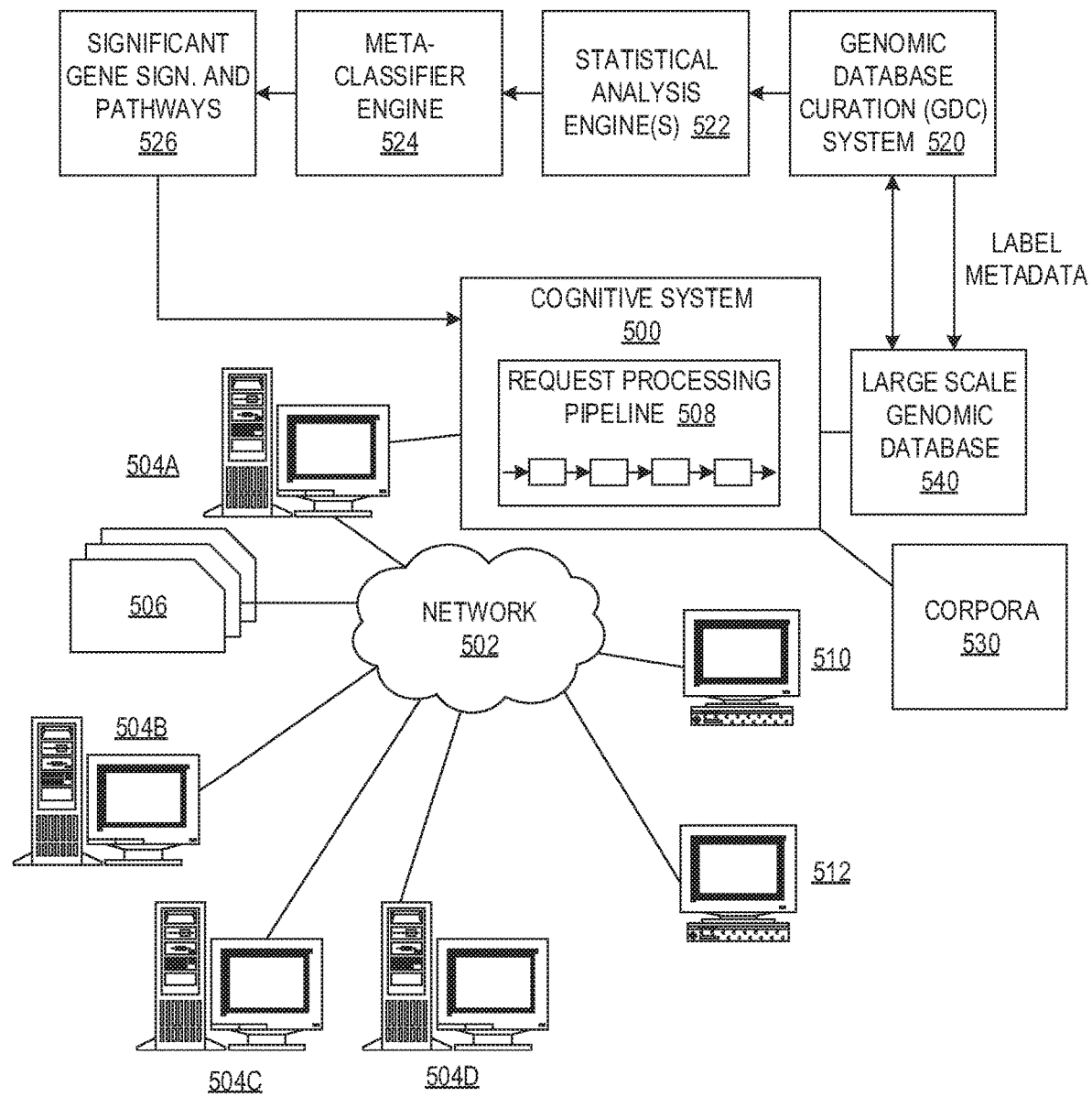
FIG. 5 depicts a schematic diagram of one illustrative embodiment of a cognitive healthcare system in a computer network.
Figure 6:
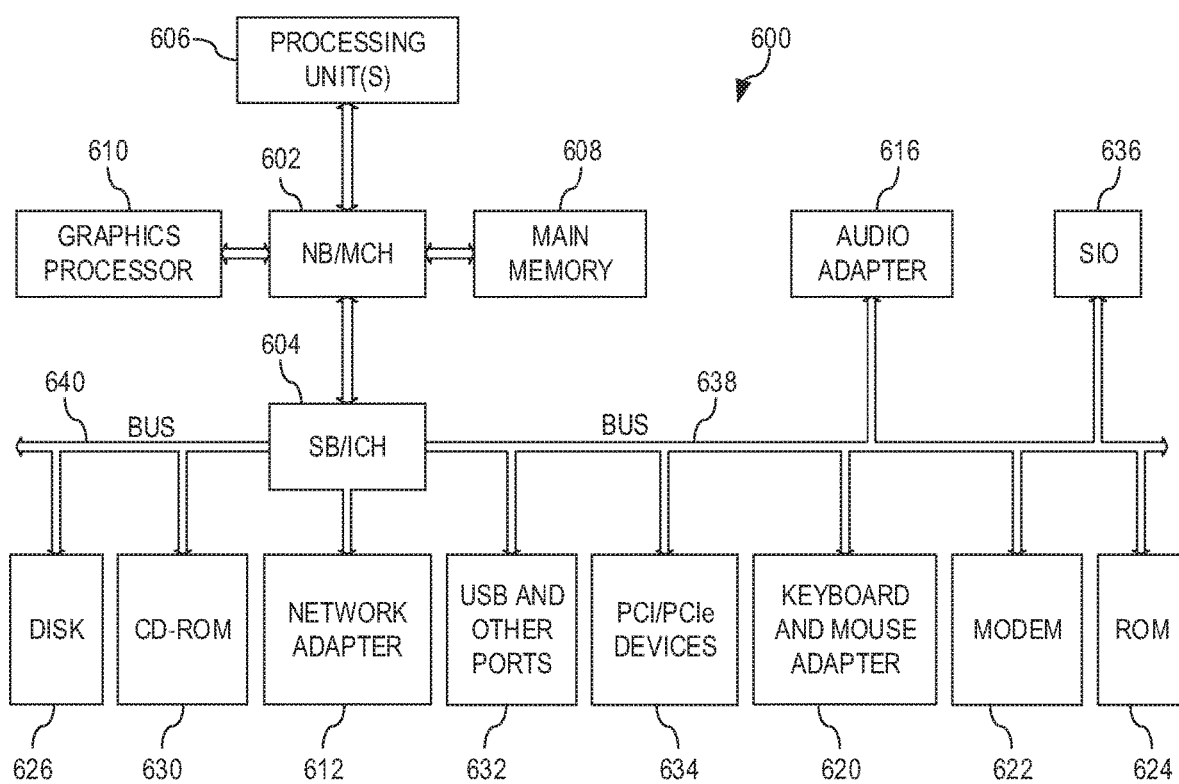
FIG. 6 is a block diagram of an example data processing system in which aspects of the illustrative embodiments are implemented.

Thus, the illustrative embodiments may be utilized in many different types of data processing environments. In order to provide a context for the description of the specific elements and functionality of the illustrative embodiments, FIGS. 5-6 are provided hereafter as example environments in which aspects of the illustrative embodiments may be implemented. It should be appreciated that FIGS. 5-6 are only examples and are not intended to assert or imply any limitation with regard to the environments in which aspects or embodiments of the present invention may be implemented. Many modifications to the depicted environments may be made without departing from the spirit and scope of the present invention.

While FIG. 5 illustrates the mechanisms of the illustrative embodiments being utilized with a cognitive computing system 500, it should be appreciated that other types of analysis computing systems and/or viewer computing systems may be used with the mechanisms of the illustrative embodiments. For example, rather than performing cognitive computing operations based on the significant gene signature and pathway information generated by the meta-classifier engine of the illustrative embodiments, the computing system may instead provide a viewer application through which a user may view the significant genetic signatures and pathways for particular diseases and/or drug agents, and/or view and search the automatically curated large scale genomic database. Such viewing and searching may be facilitated by one or more graphical user interfaces specifically configured and generated to provide the significant gene signature and pathway information for diseases and/or drug agents, entries in the automatically curated large scale genomic database, and or provide a search engine for searching the curated large scale genomic database.

With regard to the cognitive computing system implementation depicted in FIG. 5, an example schematic diagram of one illustrative embodiment of a cognitive computing system 500 implementing a request processing pipeline 508 is provided, where in some embodiments the pipeline 508 may be a question answering (QA) pipeline. For purposes of the present description, it will be assumed that the request processing pipeline 508 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety. The cognitive computing system 500 is implemented on one or more computing devices 504A-D (comprising one or more processors and one or more memories, and potentially any other computing device elements generally known in the art including buses, storage devices, communication interfaces, and the like) connected to the computer network 502. For purposes of illustration only, FIG. 5 depicts the cognitive computing system 500 being implemented on computing device 504A only, but as noted above the cognitive system 500 may be distributed across multiple computing devices, such as a plurality of computing devices 504A-D. The network 502 includes multiple computing devices 504A-D, which may operate as server computing devices, and 510-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive computing system 500 and network 502 enables question processing and answer generation (QA) functionality for one or more cognitive system users via their respective computing devices 510-112. In other embodiments, the cognitive computing system 500 and network 502 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 500 may be used with components, systems, subsystems, and/or devices other than those that are depicted herein.

The cognitive computing system 500 is configured to implement a request processing pipeline 508 that receive inputs from various sources. The requests may be posed in the form of a natural language question, natural language request for information, natural language request for the performance of a cognitive operation, or the like. For example, the cognitive computing system 500 receives input from the network 502, a corpus or corpora of electronic documents 506, cognitive computing system users, and/or other data and other possible sources of input. In one embodiment, some or all of the inputs to the cognitive computing system 500 are routed through the network 502. The various computing devices 504A-D on the network 502 include access points for content creators and cognitive system users. Some of the computing devices 504A-D include devices for a database storing the corpus or corpora of data 506 (which is shown as a separate entity in FIG. 5 for illustrative purposes only). Portions of the corpus or corpora of data 506 may also be provided on one or more other network attached storage devices, in one or more databases, or other computing devices not explicitly shown in FIG. 5. The network 502 includes local network connections and remote connections in various embodiments, such that the cognitive computing system 500 may operate in environments of any size, including local and global, e.g., the Internet.

In one embodiment, the content creator creates content in a document of the corpus or corpora of data 506 for use as part of a corpus of data with the cognitive computing system 500. The document includes any file, text, article, or source of data for use in the cognitive system 500. Cognitive computing system users access the cognitive computing system 500 via a network connection or an Internet connection to the network 502, and input questions/requests to the cognitive computing system 500 that are answered/processed based on the content in the corpus or corpora of data 506. In one embodiment, the questions/requests are formed using natural language. The cognitive computing system 500 parses and interprets the question/request via a pipeline 508, and provides a response to the cognitive system user, e.g., cognitive system user 510, containing one or more answers to the question posed, response to the request, results of processing the request, or the like. In some embodiments, the cognitive computing system 500 provides a response to users in a ranked list of candidate answers/responses while in other illustrative embodiments, the cognitive computing system 500 provides a single final answer/response or a combination of a final answer/response and ranked listing of other candidate answers/responses.

The cognitive computing system 500 implements the pipeline 508 which comprises a plurality of stages for processing an input question/request based on information obtained from the corpus or corpora of data 506. The pipeline 508 generates answers/responses for the input question or request based on the processing of the input question/request and the corpus or corpora of data 506.

In some illustrative embodiments, the cognitive computing system 500 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 506. Based on the application of the queries to the corpus or corpora of data 506, a set of hypotheses, or candidate answers/responses to the input question/request, are generated by looking across the corpus or corpora of data 506 for portions of the corpus or corpora of data 506 (hereafter referred to simply as the corpus 506) that have some potential for containing a valuable response to the input question/response (hereafter assumed to be an input question). The pipeline 508 of the IBM Watson™ cognitive system then performs deep analysis on the language of the input question and the language used in each of the portions of the corpus 506 found during the application of the queries using a variety of reasoning algorithms.

The scores obtained from the various reasoning algorithms are then weighted against a statistical model that summarizes a level of confidence that the pipeline 508 of the IBM Watson™ cognitive system 500, in this example, has regarding the evidence that the potential candidate answer is inferred by the question. This process is be repeated for each of the candidate answers to generate ranked listing of candidate answers which may then be presented to the user that submitted the input question, e.g., a user of client computing device 510, or from which a final answer is selected and presented to the user. More information about the pipeline 508 of the IBM Watson™ cognitive system 500 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 500 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis.

As shown in FIG. 5, the cognitive computing system 500 further operates on the large scale genomic database 540 which is automatically curated by the genomic database curation (GDC) system 520 of the illustrative embodiments and the significant gene signature and/or pathway information generated by the meta-classifier engine 524 of the illustrative embodiments. That is, as noted above, the request processing pipeline 508 operates on one or more corpora of electronic documentation to provide candidate answers and/or evidence for evaluating candidate answers. As part of this one or more corpora, the automatically curated large scale genomic database, comprising the original large scale genomic database 540 in combination with the label metadata generated by the GDC system 520, is provided as additional information upon which such candidate answers may be generated and/or evidential analysis may be performed. Similarly, the significant gene signatures and/or pathways may also be provided as part of one or more corpora for generating candidate answers and performing evidential analysis.

The GDC system 520, as previously described above, uses a small subset of the uncurated large scale genomic database 540 to generate a ground truth database that is used to train one or more classification engines, e.g., neural network models, to perform classification on input datasets. Once trained, the classification engine(s) are executed or applied to the large scale genomic database 540 to generate label metadata that is then associated with their corresponding datasets in the large scale genomic database 540 or integrated with the metadata of these datasets to generate an automatically curated large scale genomic database 540 that is accessed by the cognitive system 500 to perform its cognitive operations. The curated datasets of the large scale genomic database 540 are also provided to one or more statistical analysis engines 522 which identify the statistically significant gene signatures and/or pathways associated with the individual datasets. These curated datasets and statistical information are provided to the meta-classifier engine 524 which then merges the datasets for the various diseases and/or drug agents and generates an output indicating the significant gene signatures and/or pathways for these various diseases and/or drug agents 526. This information, like the automatically curated large scale genomic database 540, may be used as a basis for generating candidate answers and/or performing evidential scoring of candidates answers by the cognitive computing system 500.

Based on the various sources of information 506, 530, 540, 526, etc., the cognitive computing system 500 may perform a variety of different cognitive computing operations based on the desired implementation. In some cases, this cognitive operation may be to provide a graphical user interface detailing significant gene signatures and/or pathways for specified diseases and/or drug agents of interest to the particular user, e.g., specified in an input question or request received from a client computing device 510. In other illustrative embodiments, this cognitive computing system 500 may be specifically configured to implement a patient diagnostics system, medical treatment recommendation systems, medical research system, patient electronic medical record (EMR) evaluation for various purposes, such as for identifying patients that are suitable for a medical trial or a particular type of medical treatment, or the like. Thus, the cognitive system 500 may be a healthcare cognitive system 500 that operates in the medical or healthcare type domains and which may process requests for such healthcare operations via the request processing pipeline 508 input as either structured or unstructured requests, natural language input questions, or the like As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 6 is provided as an example of one type of data processing system in which aspects of the present invention may be implemented. Many other types of data processing systems may be likewise configured to specifically implement the mechanisms of the illustrative embodiments.

As shown in FIG. 6, data processing system 600 is an example of a computer, such as server 504A-D or client 510 in FIG. 5, in which computer usable code or instructions implementing the processes for illustrative embodiments of the present invention are located. In one illustrative embodiment, FIG. 6 represents a server computing device, such as a server 504A-D, which implements a cognitive system 500 and request processing pipeline 508 augmented to include the additional mechanisms of the illustrative embodiments described hereafter.

In the depicted example, data processing system 600 employs a hub architecture including North Bridge and Memory Controller Hub (NB/MCH) 602 and South Bridge and Input/Output (I/O) Controller Hub (SB/ICH) 604. Processing unit 606, main memory 608, and graphics processor 610 are connected to NB/MCH 602. Graphics processor 610 is connected to NB/MCH 602 through an accelerated graphics port (AGP).

In the depicted example, local area network (LAN) adapter 612 connects to SB/ICH 604. Audio adapter 616, keyboard and mouse adapter 620, modem 622, read only memory (ROM) 624, hard disk drive (HDD) 626, CD-ROM drive 630, universal serial bus (USB) ports and other communication ports 632, and PCI/PCIe devices 634 connect to SB/ICH 604 through bus 638 and bus 640. PCI/PCIe devices may include, for example, Ethernet adapters, add-in cards, and PC cards for notebook computers. PCI uses a card bus controller, while PCIe does not. ROM 624 may be, for example, a flash basic input/output system (BIOS).

HDD 626 and CD-ROM drive 630 connect to SB/ICH 604 through bus 640. HDD 626 and CD-ROM drive 630 may use, for example, an integrated drive electronics (IDE) or serial advanced technology attachment (SATA) interface. Super I/O (SIO) device 636 is connected to SB/ICH 604.

An operating system runs on processing unit 606. The operating system coordinates and provides control of various components within the data processing system 600 in FIG. 6. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 600.

As a server, data processing system 600 may be, for example, an IBM® eServer™ System p° computer system, running the Advanced Interactive Executive (AIX®) operating system or the LINUX® operating system. Data processing system 600 may be a symmetric multiprocessor (SMP) system including a plurality of processors in processing unit 606. Alternatively, a single processor system may be employed.

Instructions for the operating system, the object-oriented programming system, and applications or programs are located on storage devices, such as HDD 626, and are loaded into main memory 608 for execution by processing unit 606. The processes for illustrative embodiments of the present invention are performed by processing unit 606 using computer usable program code, which is located in a memory such as, for example, main memory 608, ROM 624, or in one or more peripheral devices 626 and 630, for example.

A bus system, such as bus 638 or bus 640 as shown in FIG. 6, is comprised of one or more buses. Of course, the bus system may be implemented using any type of communication fabric or architecture that provides for a transfer of data between different components or devices attached to the fabric or architecture. A communication unit, such as modem 622 or network adapter 612 of FIG. 6, includes one or more devices used to transmit and receive data. A memory may be, for example, main memory 608, ROM 624, or a cache such as found in NB/MCH 602 in FIG. 6.

Those of ordinary skill in the art will appreciate that the hardware depicted in FIGS. 5 and 6 may vary depending on the implementation. Other internal hardware or peripheral devices, such as flash memory, equivalent non-volatile memory, or optical disk drives and the like, may be used in addition to or in place of the hardware depicted in FIGS. 5 and 6. Also, the processes of the illustrative embodiments may be applied to a multiprocessor data processing system, other than the SMP system mentioned previously, without departing from the spirit and scope of the present invention.

Moreover, the data processing system 600 may take the form of any of a number of different data processing systems including client computing devices, server computing devices, a tablet computer, laptop computer, telephone or other communication device, a personal digital assistant (PDA), or the like. In some illustrative examples, data processing system 600 may be a portable computing device that is configured with flash memory to provide non-volatile memory for storing operating system files and/or user-generated data, for example. Essentially, data processing system 600 may be any known or later developed data processing system without architectural limitation.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, performed by a data processing system comprising at least one processor and at least one memory, the at least one memory comprising instructions executed by the at least one processor to configure the at least one processor to implement a genomic database curation system, wherein the genomic database curation (GDC) system operates to perform the method which comprises:
    generating, by the GDC system, a ground truth database based on both a training subset of datasets, from an uncurated genomic database, and label metadata for the training subset;
    automatically training, by automatically executed training logic of the GDC system, a plurality of classification computer models of the GDC system based on the training subset and the ground truth database at least by executing machine learning on the plurality of classification computer models, to thereby generate a plurality of trained classification computer models;
    automatically executing, by the GDC system, the plurality of trained classification computer models on the uncurated genomic database to generate an automatically curated genomic database; and
    generating, by a meta-classifier computer model, an output specifying at least one of gene signatures or gene pathways for at least one of diseases or drug agents based on the automatically curated genomic database,
    wherein each classification computer model, in the plurality of classification computer models, during the automatic training of the classification computer model, iteratively executes on word embedding features of the training subset to perform a computer regression operation and train the classification computer model based on results of the computer regression operation and the ground truth database, wherein each classification computer model is configured and automatically trained to generate a different type of classification output from each other classification computer model in the plurality of classification computer models, and wherein the types of classification outputs comprise at least one disease type classification, at least one drug agent type classification, and at least one disease state binary class label type classification.

2. The method of claim 1, wherein the uncurated genomic database comprises a plurality of gene expression signature datasets, each gene expression signature dataset being associated with a genomic study, and wherein each gene expression signature dataset comprises one or more sample entries.

3. The method of claim 2, wherein the training subset of datasets is a subset of the gene expression signature datasets, and wherein the method further comprises pre-curating each gene expression signature dataset in the training subset to extract a subset of features from the content of the gene expression signature dataset for correlation with the label metadata.

4. The method of claim 1, wherein the uncurated genomic database comprises gene expression signature datasets obtained from a plurality of different source computing devices, and wherein a plurality of the gene expression signature datasets from different source computing devices have differently formatted free-text portions of metadata and sample information content from each other.

5. The method of claim 1, wherein the plurality of classification computer model comprises:
    one or more first classification computer models, each first classification computer model being associated with a different disease than other first classification computer models in the one or more first classification computer models, wherein each first classification computer model executes on word embeddings of an input dataset and automatically generates a first output specifying a first classification value indicating whether a study associated with an input dataset is directed to identifying a particular disease that the first classification computer model is machine learning trained to identify in input features associated with studies;

one or more second classification computer models, each second classification computer model being associated with a different drug agent than other second classification computer models in the one or more second classification computer models, wherein each second classification computer model executes on the word embeddings of the input dataset and automatically generates a second output specifying a second classification value indicating whether a study associated with the input dataset involves the corresponding drug agent that the second classification computer model is machine learning trained to identify in the input features associated with studies;

a third classification computer model that executes on word embeddings of the input dataset and automatically generates a third output specifying a third classification value indicating whether one or more particular samples referenced in the input dataset has a corresponding disease state or not, to thereby generate a disease state binary class label; and one or more fourth classification computer models, wherein each fourth classification computer model executes and automatically generates a fourth output specifying a results of evaluating samples at each time point after a drug agent administration.

6. The method of claim 5, wherein each fourth classification computer model of the one or more fourth classification computer models evaluates a half maximal inhibitory concentration ($IC_{50}$) value of a drug agent at a time point after administration of the drug agent.

7. The method of claim 1, wherein automatically executing the at least one trained classification computer model on the uncurated genomic database to generate an automatically curated genomic database comprises, for each uncurated dataset in the uncurated genomic database:

executing computer natural language processing on the uncurated dataset to extract that extracts features from the uncurated dataset;

processing, by the at least one trained classification computer model, the extracted features from the uncurated dataset to generate classification label metadata for the uncurated dataset; and storing the classification label metadata in association with the uncurated dataset to thereby generate a curated dataset.

8. The method of claim 1, wherein generating, by the meta-classifier computer model, the output comprises:

identifying a subset of curated datasets in the curated genomic database that corresponds to at least one of a particular disease or a particular drug agent; and performing a statistical analysis of the subset of curated datasets to identify gene signatures associated with the particular disease or drug agent.

9. The method of claim 8, wherein generating, by the meta-classifier computer model, the output further comprises:

combining, via one or more hierarchical random effect models of the meta-classifier computer model, separate datasets in the subset of curated datasets by merging individual signals of gene signatures of the individual datasets based on statistical scores associated with each of the gene signatures of the individual datasets and weight values associated with each of the individual datasets, wherein the weight values are based on a variance within each of the individual datasets.

10. The method of claim 8, further comprising:

receiving, from a client computing device, a user request specifying at least one of a disease or drug agent criteria for identifying gene signatures or gene pathways, wherein the subset of curated datasets is a subset of curated datasets corresponding to at least one of a disease or drug agent specified in the at least one of a disease or drug agent criteria of the user request, and wherein generating the output further comprises generating a view in a graphical user interface through which a user views the identified gene signatures or gene pathways associated with the disease or drug agent criteria specified in the user request, based on results of the statistical analysis of the subset of curated datasets.

11. A computer program product comprising a non-transitory computer readable storage medium having a computer readable program stored therein, wherein the computer readable program, when executed on a computing device, causes the computing device to implement a genomic database curation system, wherein the genomic database curation (GDC) system operates to:

generate a ground truth database based on both a training subset of datasets, from an uncurated genomic database, and label metadata for the training subset;

automatically train, by automatically executed training logic of the GDC system, a plurality of classification computer models of the GDC system based on the training subset and the ground truth database at least by executing machine learning on the plurality of classification computer models, to thereby generate a plurality of trained classification computer models;

automatically execute the plurality of trained classification computer models on the uncurated genomic database to generate an automatically curated genomic database; and generate, by a meta-classifier computer model, an output specifying at least one of gene signatures or gene pathways for at least one of diseases or drug agents based on the automatically curated genomic database, wherein each classification computer model, in the plurality of classification computer models, during the automatic training of the classification computer model, iteratively executes on word embedding features of the training subset to perform a computer regression operation and train the classification computer model based on results of the computer regression operation and the ground truth database, wherein each classification computer model is configured and automatically trained to generate a different type of classification output from each other classification computer model in the plurality of classification computer models, and wherein the types of classification outputs comprise at least one disease type classification, at least one drug agent type classification, and at least one disease state binary class label type classification.

12. The computer program product of claim 11, wherein the uncurated genomic database comprises a plurality of gene expression signature datasets, each gene expression signature dataset being associated with a genomic study, and wherein each gene expression signature dataset comprises one or more sample entries.

13. The computer program product of claim 12, wherein the training subset of datasets is a subset of the gene expression signature datasets, and wherein the method further comprises pre-curating each gene expression signature dataset in the training subset to extract a subset of features from the content of the gene expression signature dataset for correlation with the label metadata.

14. The computer program product of claim 11, wherein the uncurated genomic database comprises gene expression signature datasets obtained from a plurality of different source computing devices, and wherein a plurality of the gene expression signature datasets from different source computing devices have differently formatted free-text portions of metadata and sample information content from each other.

15. The computer program product of claim 11, wherein the at least one classification computer model comprises:
  one or more first classification computer models, each first classification computer model being associated with a different disease than other first classification computer models in the one or more first classification computer models, wherein each first classification computer model executes on word embeddings of an input dataset and automatically generates a first output specifying a first classification value indicating whether a study associated with an input dataset is directed to identifying a particular disease that the first classification computer model is machine learning trained to identify in input features associated with studies;
  one or more second classification computer models, each second classification computer model being associated with a different drug agent than other second classification computer models in the one or more second classification computer models, wherein each second classification computer model executes on the word embeddings of the input dataset and automatically generates a second output specifying a second classification value indicating whether a study associated with the input dataset involves the corresponding drug agent that the second classification computer model is machine learning trained to identify in the input features associated with studies;
  a third classification computer model that executes on word embeddings of the input dataset and automatically generates a third output specifying a third classification value indicating whether one or more particular samples referenced in the input dataset has a corresponding disease state or not, to thereby generate a disease state binary class label; and
  one or more fourth classification computer models, wherein each fourth classification computer model executes and automatically generates a fourth output specifying a results of evaluating samples at each time point after a drug agent administration.

16. The computer program product of claim 15, wherein each fourth classification computer model of the one or more fourth classification computer models evaluates a half maximal inhibitory concentration ($IC_{50}$) value of a drug agent at a time point after administration of the drug agent.

17. The computer program product of claim 11, wherein the computer readable program further causes the GDC system to automatically execute the at least one trained classification computer model on the uncurated genomic database to generate an automatically curated genomic database comprises, for each uncurated dataset in the uncurated genomic database:
  executing computer natural language processing on the uncurated dataset that extracts features from the uncurated dataset;
  processing, by the at least one trained classification computer model, the extracted features from the uncurated dataset to generate classification label metadata for the uncurated dataset; and
  storing the classification label metadata in association with the uncurated dataset to thereby generate a curated dataset.

18. The computer program product of claim 11, wherein the computer readable program further causes the GDC system to generate, by the meta-classifier computer model, the output at least by:
  identifying a subset of curated datasets in the curated genomic database that corresponds to at least one of a particular disease or a particular drug agent; and
  performing a statistical analysis of the subset of curated datasets to identify gene signatures associated with the particular disease or drug agent.

19. The computer program product of claim 18, wherein the computer readable program further causes the GDC system to generate, by the meta-classifier computer model, the output further at least by:
  combining, via one or more hierarchical random effect models of the meta-classifier computer model, separate datasets in the subset of curated datasets by merging individual signals of gene signatures of the individual datasets based on statistical scores associated with each of the gene signatures of the individual datasets and weight values associated with each of the individual datasets, wherein the weight values are based on a variance within each of the individual datasets.

20. An apparatus comprising:
  a processor; and
  a memory coupled to the processor, wherein the memory comprises instructions which, when executed by the processor, cause the processor to implement a genomic database curation system, wherein the genomic database curation (GDC) system operates to:
  generate a ground truth database based on both a training subset of datasets, from an uncurated genomic database, and label metadata for the training subset;
  automatically train, by automatically executed training logic of the GDC system, a plurality of classification computer models of the GDC system based on the training subset and the ground truth database at least by executing machine learning on the plurality of classification computer models, to thereby generate a plurality of trained classification computer models;
  automatically execute the plurality of trained classification computer models on the uncurated genomic database to generate an automatically curated genomic database; and
  generate, by a meta-classifier computer model, an output specifying at least one of gene signatures or gene pathways for at least one of diseases or drug agents based on the automatically curated genomic database, wherein each classification computer model, in the plurality of classification computer models, during the automatic training of the classification computer model, iteratively executes on word embedding features of the training subset to perform a computer regression operation and train the classification computer model based on results of the computer regression operation and the ground truth database, wherein each classification computer model is configured and automatically trained to generate a different type of classification output from each other classification computer model in the plurality of classification computer models, and wherein the types of classification outputs comprise at least one disease type classification, at least one drug agent type classification, and at least one disease state binary class label type classification.

* * * * *